United States Patent [19]

Stilz et al.

[11] 4,033,941
[45] July 5, 1977

[54] PROCESS FOR PURIFYING GLUCAGON

[75] Inventors: John G. Stilz; Richard L. Jackson, both of Indianapolis, Ind.

[73] Assignee: Eli Lilly and Company, Indianapolis, Ind.

[22] Filed: Dec. 17, 1975

[21] Appl. No.: 641,419

[52] U.S. Cl. .................. 260/112.5 R; 260/112.7
[51] Int. Cl.² ................................. C07C 103/52
[58] Field of Search ............... 260/112.5 R, 112.7

[56] References Cited

UNITED STATES PATENTS

| | | | |
|---|---|---|---|
| 3,715,345 | 2/1973 | Smith | 260/112.7 |
| 3,875,138 | 4/1975 | Jackson | 260/112.5 R |
| 3,878,186 | 4/1975 | Jackson | 260/112.7 |

Primary Examiner—Delbert R. Phillips
Attorney, Agent, or Firm—William E. Maycock; Everet F. Smith

[57] ABSTRACT

Glucagon is purified by gel filtration at a pH of from about 9 to about 11.

12 Claims, 1 Drawing Figure

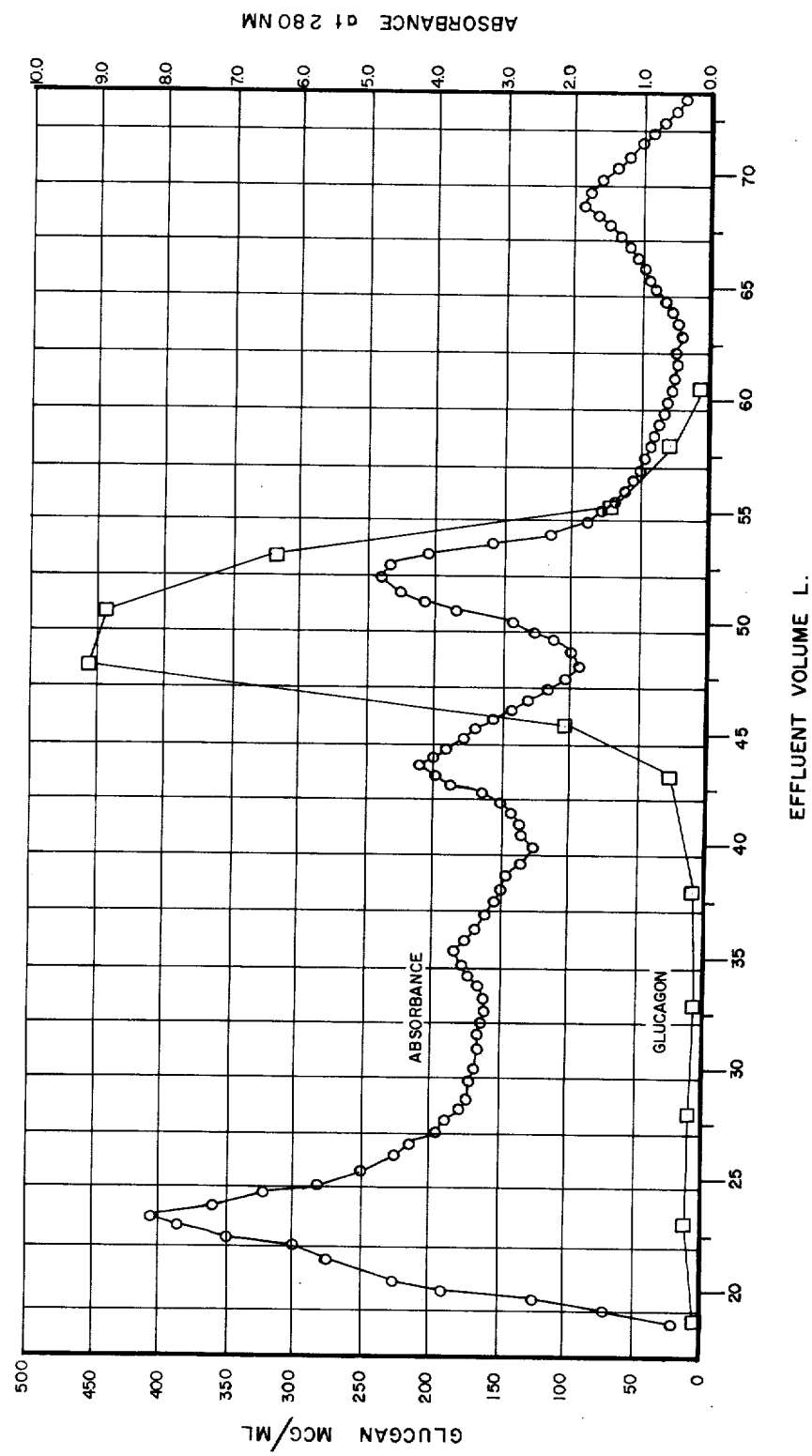

PROCESS FOR PURIFYING GLUCAGON

BACKGROUND OF THE INVENTION

This invention relates to a glucagon. More particularly, this invention relates to a process for purifying glucagon.

Shortly after the discovery of insulin in 1921 by Banting and Best, several researchers [Murlin, et. al., *J. Biol. Chem.*, 56, 252 (1923) and Kimball and Murlin, *J. Biol. Chem.*, 58, 337 (1924)] noted that a hyperglycemic response was obtained with certain pancreatic extracts of insulin. The factor responsible for the hyperglycemic response was named glucagon. Subsequent research efforts resulted in the purification and crystallization of glucagon; see Staub, et al., *Science*, 117, 628 (1953) and *J. Biol. Chem.*, 214, 619 (1955). Structurally, glucagon is a single polypeptide chain of 29 amino acids. The amino acid sequence of porcine glucagon was established by Bromer, et al., *J. Am. Chem. Soc.*, 79, 2807 (1957).

As already noted, glucagon causes a hyperglycemic response; i.e., an increase in the concentration of glucose in the blood. In this respect, glucagon is in dynamic opposition to insulin which causes a hypoglycemic response, a decrease in the concentration of blood glucose. Consequently, an important use of glucagon is in the treatment of insulin-induced hypoglycemia when hypertonic glucose solution is not available.

Glucagon also has been shown to exhibit a positive inotropic effect; see Farah and Tuttle, *J. Pharmacol. Exptl. Therap.*, 29, 49 (1960). Thus, the administration of glucagon has been shown to produce an increase in the contractal force of the heart. This has led to an extensive use of glucagon in the treatment of hypodynamic heart disorders in which an increase in cardiac contractile force is required [Van der Ark, et. al., *Amer. Heart J.*, 79, 481 (1970)].

Additionally, it has been recognized that glucagon exhibits various other kinds of biological activity. For example, glucagon has been used to relax the duodenum for X-ray visualization in hypotonic duodenography [Miller, et al., *Radiology*, 108, 35 (1973)]. Glucagon also is active as a diuretic, as a bronchodilator, in reducing gastric secretion, and in reducing the level of blood lipids and blood cholesterol. Finally, glucagon has been used in the treatment of pancreatitis [Stremmel, *Pharmakotherapie In Kurze*, 116, 69 (1974)].

The above-described recognized practical uses of glucagon are placing increased demands on the availability and purity of glucagon.

It is well known that both insulin and glucagon are produced within the pancreas. While the isolation and purification of insulin have reached a high degree of sophistication, prior art procedures for isolating and purifying glucagon still present various problems, particularly with respect to purity, glucagon degradation, and recovery efficiency. Such problems at one time were due in part to the close relationship between insulin and glucagon. Improvements in insulin purification procedures, however, have eliminated or minimized the contribution to such problems from insulin processing procedures.

At the present time, such problems are associated primarily with the prior art procedures for purifying glucagon. For example, fibril formation is carried out at a low pH, typically about pH 2.0, an environment which contributes to increased glucagon hydrolysis. The products of hydrolysis in general exhibit reduced activity. For example, desamido glucagon possesses only about 60 percent of the hormonal activity of glucagon. In addition, fibril formation is dependent upon glucagon purity; as purity decreases, fibril formation becomes increasingly difficult or even impossible.

Because glucagon has a tendency to gel and to form fibrils in acidic solutions, chromatographic procedures involving acidic glucagon solutions tend to experience glucagon losses from the gelation and precipitation of glucagon in the column. Furthermore, glucagon tends to aggregate in acidic solutions, thereby significantly reducing the selectivity and effectiveness of gel filtration (gel exclusion chromatography) under acidic conditions.

SUMMARY OF THE INVENTION

It therefore is an object of the present invention to provide a process for the purification of glucagon which eliminates or minimizes many of the problems associated with prior art procedures.

A further object of the present invention is to provide a process for purifying glucagon under more mild conditions, but which is more selective and gives greater glucagon recovery, than prior art procedures.

Yet another object is to provide a process for purifying glucagon which utilizes gel filtration without the usual prior art problems associated therewith.

These and other objects will be apparent to those skilled in the art from a consideration of the specification and claims which follow.

According to the present invention, glucagon is purified by the process which comprises the steps of swelling a gel having in the dry state a water regain of at least about 4 percent by weight and particle sizes smaller than about 100 microns in diameter; packing a column with the swollen gel; adding to the packed column an aqueous solution, having a pH of from about 9 to about 11, of glucagon having a purity of at least about 0.1 percent; and eluting the glucagon from the column, at a temperature of from about 4° to about 40° C, with an aqueous eluant having a pH within the same range as that of the glucagon column feed solution. The glucagon column feed solution will contain at least about 0.01 mg of glucagon per ml of solution and less than about 10 percent, weight per volume, total protein solids. The total amount of glucagon added to the column is that amount which is sufficient to provide a column loading of from about 0.01 to about 5 g per liter of bed volume.

It will be recognized by those having ordinary skill in the art that such terms as "purifying," "purification," and the like as used herein, are to be construed broadly; i.e., such terms mean that the impure glucagon, in whatever form, whether as a solid or in aqueous solution, becomes enriched in glucagon content relative to total protein solids. Thus, glucagon purity, defined as the ratio of glucagon to total protein solids (usually expressed as percent purity) is increased.

Interestingly, hydrolysis of glucagon to monodesamido glucagon while carrying out the process of the present invention is not a problem, even though the ready hydrolysis of glucagon under alkaline conditions is well known; see, e. g., Annable, *Acta Endocrinologica*, 77, 706 (1974).

BRIEF DESCRIPTION OF THE DRAWING

The drawing is the elution diagram or profile which is characteristic of the process of the present invention as exemplified by Example 1. The diagram is a plot of both eluate optical density and glucagon content versus effluent (or eluate) volume.

DETAILED DESCRIPTION OF THE INVENTION

Briefly, gel filtration is a chromatographic procedure for separating materials, e.g., proteins, on the basis of molecular size. In this method, materials are separated on a column containing a gel which has been cross-linked in such a manner that pores are formed within each gel particle. These pores have a finite, measurable volume which is directly proportional to the degree of swelling of the gel and inversely proportional to the degree of cross-linking. Because smaller molecules have more complete access to these pores than larger molecules, the progress of smaller molecules through the column is impeded relative to larger molecules which have only partial or no access to the pores.

In general, any water-swellable gel suitable for use with protein solutes can be employed in the process of the present invention. However, such a gel shall have in the dry or nonswollen state a water regain of at least about 4 percent by weight, based on the weight of dry gel, and particle diameters smaller than about 100 microns. Preferably, the water regain of the gel will be in the range of from about 4 to about 98 percent, and most preferably from about 5 to about 20 percent. Preferably, the diameters of the dry gel particles will be smaller than about 80 microns; a particularly useful range of particle diameters is from about 20 to about 80 microns.

Examples of suitable gels include, among others, starch (including maize starch), crosslinked galactomannan, crosslinked dextran, agar or agarose, polyacrylamides, copolymers of acrylamide and methylene bis-acrylamide, copolymers of methylene bis-acrylamide with vinyl ethyl carbitol and with vinyl pyrrolidone, and the like. The preferred gels are crosslinked dextrans, such as the Sephadex series from Pharmacia Fine Chemicals, Inc., Piscataway, N.J.

The type of column employed in the process of the present invention is not critical. The choice of column height, diameter, or configuration will depend upon the operating parameters desired. Of course, as column height increases the flow rate decreases; stated differently, column back-pressure is directly proportional to column height. For this reason, a stacked column configuration is preferred, such as the Pharmacia Sectional Column KS-370. For normal production purposes, a stack of from four to six sections serves quite well.

As an approximation, satisfactory glucagon purification can be accomplished at column loadings of from about 0.08 to about 3.1 of glucagon per liter of bed volume, which range is most preferred. However, column loadings generally can range from about 0.01 to about 5 g per liter of bed volume. Optimum conditions for any given column can be readily determined.

The gel can be swollen and the column packed with the swollen gel by any of the various methods known to those skilled in the art. In general, the gel will be swollen in the eluting medium. Alternatively, the gel can be swollen in 30 percent agueous ethanol, the fines decanted, and the swelling medium replaced with eluting medium.

Essentially any source of impure glucagon can be employed, provided that such source contains at least about 0.1 pecent, preferably at least about 1 percent, by weight glucagon. Thus, such source can vary from crude pancreas protein fractions to partially-purified glucagon crystals.

The impure glucagon can be dissolved in acidified water, typically at pH 3. The pH then is adjusted to 9–11 as desired with dilute aqueous base or organic buffer. Alternatively, and preferably, the impure glucagon is dissolved in an alkaline aqueous medium at pH 9–11. Suitable bases include sodium hydroxide, potassium hydroxide, lithium hydroxide, ammonium hydroxide, and the like. Sodium hydroxide is preferred. Examples of suitable organic buffers include glycine-sodium hydroxide, tris(hydroxymethyl) aminomethane, and the like. If necessary, insoluble material can be removed by any convenient means. As already stated, the glucagon column feed solution pH will be in the range of from about 9 to about 11. The preferred solution pH range is from about 9.0 to about 10.5. While the glucagon column feed solution pH and the pH of the eluant need not be identical, large differences preferably are avoided.

The glucagon column feed solution thus obtained should contain at least about 0.01 mg, preferably at least about 0.05 mg, and most preferably at least about 0.5 mg of glucagon per ml. Such solution should also contain less than about 10 percent, weight per volume, total protein solids. Preferably, total protein solids will be less than about 8 percent, most preferably less than about 6 percent, weight per volume. If desired, the glucagon column feed solution can be buffered, although buffering is not necessary. Optionally, and preferably, the glucagon column feed solution can contain a divalent metal ion chelating agent and a stabilizing reagent as discussed hereinafter with respect to the eluant.

For satisfactory results, the impure glucagon should be dissolved in a volume of solvent which is less than the separation volume, discussed hereinbelow.

In chromatography, the distribution coefficient, $K_d$, is defined as the ratio of the concentration of solute in the mobile phase to the concentration of solute in the stationary phase. In gel filtration, the mobile phase is the solvent moving in the void space between gel particles and the stationary phase is the solvent imbided in the gel particles, i.e., trapped in the pores within each gel particle. Thus, $k_d$ indicates that fraction of imbibed solvent which is penetratable by a solute.

In terms of $k_d$, the solution volume, $V_r$, of a solute can be expressed by the equation.

$$V_r = V_o + K_d \cdot V_i$$

where $V_o$ is the void volume of the column and $V_i$ is the volume of imbibed solvent. Solving for $K_d$, the equation becomes $$K_d = (V_r - V_o)/V_i$$

If the density of water is assumed to be unity, $V_i = aW_r$, where $a$ is the weight of dry gel and $W_r$ is the water regain. Thus, $k_d$ becomes $$K_d = (V_r - V_o)/aW_r$$

which can be determined experimentally by those skilled in the art.

Assuming a solution contains two solutes, the elution volume for each solute is expressed as follows:

$$V_r' = V_o + K_d'V_i$$

$$V_r'' = V_o + K_d''V_i$$

The separation volume, $V_s$, is the difference between the elution volumes of the two solutes:

$$V_s = V_r'' - V_r'$$
$$V_s = (K_d'' - K_d')V_i$$

From the foregoing, it is apparent that the degree of separation of two (or more) solutes is in part dependent upon the column load. As the amount of lower molecular weight solute approaches the limit of accessible pores, the separation between two solutes necessarily must decrease. Within the load limits specified as a part of the present invention, the degree of separation can vary. In some instances, a higher column loading may be selected to balance separation versus productivity.

As already indicated, the eluant will have a pH in the range of from about 9 to about 11. The preferred pH range is from about 9.0 to about 10.5, with pH 9.5 being most preferred. Usually, the eluant will be an aqueous solution of the same type of base or organic buffer employed in the preparation of the glucagon column feed solution, with aqueous ammonium hydroxide being preferred.

Optionally, and preferably, the eluant will contain up to about 0.01 moles per liter of a divalent metal ion chelating agent and/or up to about 0.5 percent by volume of butanol as a stabilizer. The preferred amount of butanol is 0.1 percent by volume.

Such chelating agent can be represented by the following general formula:

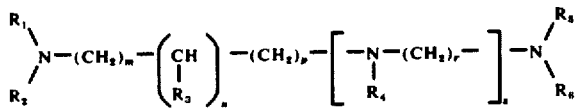

wherein $R_1$ and $R_5$ are monovalent organic radicals independently selected from the group consisting of carboxymethyl, carboxyethyl, $C_1$–$C_6$ alkyl, and $C_1$–$C_6$ hydroxyalkyl; $R_2$ and $R_6$ are monovalent organic radicals independently selected from the group consisting of carboxymethyl and carboxyethyl; $R_3$ is a monovalent radical selected from the group consisting of hydrogen, hydroxy, and $C_1$–$C_6$ alkyl; $R_4$ is a monovalent radical selected from the group consisting of hydrogen, carboxymethyl, and carboxyethyl; $m$ is an integer from 1 to 6, inclusive; $n$ is an integer which is either 0 or 1; $p$ is an integer which is either 0 or 1; $r$ is an integer from 2 to 6, inclusive; and $s$ is an integer from 0 to 2, inclusive.

Examples of chelating agents included within the above general formula include, among others, ethylenediamine-N,N,N',N'-teraacetic acid, 1,2-diaminopropane-N,N,N',N'-tetraacetic acid, 1,3-diamino-2-hydroxypropane-N,N,N',N'-tetraacetic acid, diethylenetriaminetetraacetic acid, diethylenetriaminepentaacetic acid, hexamethylenediamine-N,N,N',N'-tetraacetic acid, N-butylethylenediamine-N,N',N'-triacetic acid, N,N'-dimethyltetramethylenediamine-N,N'-diacetic acid, N-(2-hydroxyethyl)ethylenediamine-N,N',N'-triacetic acid, ethylenediamine-N,N,N',N'-tetrapropionic acid, and the like. The preferred chelating agents are polymethylenediaminetetraacetic acids; the most preferred chelating agent is ethylenediamine-N,N,N',N'-tetraacetic acid (EDTA). The chelating agent can be employed as either the free acid or an alkali metal or ammonium salt thereof.

The preferred concentration of such chelating agent is 0.001 molar.

Elution of the column is carried out at temperatures in the range of from about 4° to about 40° C. Preferably, the process temperature will be at ambient temperature or lower.

The course of elution is followed by any convenient means. A particularly useful method, however, consists of measuring the ultraviolet absorption at 280 nm of each fraction. Those fractions representing the desired purified glucagon are combined and further processed to yield high purity glucagon crystals.

In general, the choice of further processing procedures is dependent upon the purity and concentration of the glucagon present in the eluant, which choice can be made readily by one having ordinary skill in the art. As a rule, glucagon is crystallized directly from the eluant when the eluant glucagon has a purity greater than about 10 percent (weight per weight, based on total solution solids) and the concentration of glucagon in the eluant is greater than about 300 mcg per cl of eluant. Typically, glucagon is crystallized directly from the eluant at an acidic pH, i.e., at pH 4.8–5.2, preferably at pH 5.0. An alternative method of such direct crystallization of glucagon involves a zinc crystallization at pH 7.5. When the eluant glucagon purity is less than about 10 percent, the glucagon can be isolated from the eluant by a 20 percent the salt precipitation, followed by a recrystallization under acidic conditions; if desired, a second gel filtration can be carried out prior to such recrystallization. In either case, the glucagon thus obtained is of an intermediate degree of purity, and typically requires additional purification. Such additional purification can be accomplished by recrystallization from a slightly alkaline medium, i.e., at pH 7-8, ion exchange chromatography, or both. An especially useful procedure which is preferred consists of redissolving the partially purified crystalline glucagon and subjecting the resulting glucagon solution to a second gel filtration in accordance with the process of the present invention, followed by crystallization of the glucagon from the eluant under acidic or slightly alkaline conditions. By this means, glucagon having a purity in excess of 90 percent can be readily obtained. Such preferred procedure is described in greater detail hereinbelow.

In general, glucagon having a purity of from about 2 to about 5 percent by weight typically is employed in the commercial purification of glucagon via the process of the present invention. Glucagon of such purity usually consists of pancreatic protein fractions obtained from the commercial isolation and purification of insulin from bovine and porcine pancreas glands, which fractions commonly are referred to as glucagon source protein. The impure glucagon, e.g., glucagon source protein, is dissolved in acidified water having a pH of about 3, the volume of which is approximately 10 percent of the bed volume of the column to be employed. The resulting glucagon column feed solution will contain from about 3 to about 4 grams of solids per liter of bed volume and from about 0.06 to about 0.2 grams of glucagon per liter of bed volume. The column itself is equilibrated in dilute aqueous ammonia having a pH of from about 9.0 to about 10.5 and containing 0.0001 molar EDTA and 0.1 percent by volume butanol, at a temperature of 25° C. The most preferred gel is Sephadex G-50F (Pharamacia Fine Chemicals, Inc., Piscataway, N.J.).

The pH of the glucagon column feed solution then is adjusted to 9–11 with dilute aqueous base or organic buffer. Prior to introducing such solution onto the column, insoluble material can be removed by filtration, if desired. The glucagon column feed solution then is applied to the column and eluted with the pH 9.5 aqueous ammonia/EDTA/butanol described hereinbefore. Glucagon emerges with a $K_d$ of from about 0.78 to about 0.82, in a volume of eluant which is about 20–25 percent of the bed volume. The concentration of glucagon in the glucagon-containing eluant preferably will be from about 400 to about 700 mcg/ml; such glucagon will have a purity greater than about 10 percent. If further processing is to be delayed, the glucagon-containing eluant is acidified with dilute hydrochloric acid to a pH of about 3 for storage. Fractions of eluant collected before (forecut eluant fractions) and after (aftercut eluant fractions) the glucagon-containing eluant are retained for recycling to recover additional glucagon.

For further processing, the pH of the glucagon-containing eluant is adjusted to about 5 with either dilute phosphoric acid or dilute aqueous sodium or potassium hydroxide solution, as appropriate. The solution then is heated to about 60° C and filtered. The filtrate is cooled to about 5° C to induce glucagon crystallization. The glucagon crystals are harvested by any convenient means, such as centrifugation, and washed with cold 0.001 percent saline. All mother liquors and washings are retaind for reprocessing.

The glucagon crystals are dissolved in pH 9.5 aqueous ammonia/EDTA/butanol to give a solution containing from about 2 to about 6 percent (weight per volume) of such crystals, from about 0.265 to about 0.75 g of solids per liter of bed volume, and from about 0.1 to about 1.875 g of glucagon per liter of bed volume. Total solution volume will be about 2.5–7.5 percent of the bed volume. The resulting second glucagon column feed solution is applied to a second column of Sephadex G-50F, which column has a bed volume about 20 percent greater than that of the first column. The column then is eluted as described hereinbefore. The concentration of glucagon in the glucagon-containing eluant typically will be from about 500 to about 3,500 mcg/ml. Glucagon crystalizes at an eluant temperature of about 5°–10° C after the eluant pH has been adjusted to about 7–8. The glucagon crystals then are harvested in the usual manner. Again, all mother liquors and washings are retained for reprocessing.

The process of the present invention is further illustrated but not limited by the examples which follow. Example 1 is an illustration of the preferred procedure for purifying glucagon as described hereinabove, which procedure utilizes two gel filtration steps. Examples 2 and 3 are for purposes of comparison and employ a prior art process for the purification of glucagon with and without the gel filtration process of the present invention. In each example, the same source of impure glucagon was employed. Such glucagon source was derived from two protein fractions: (1) the amorphous protein fraction isolated during the preparation of zinc insulin crystals; and (2) protein remaining in citrate-buffered mother liquor after an intermediate zinc insulin crystallization, isolated by precipitation with zinc. The two protein fractions were combined, and the combination was fractionally precipitated at a pH of about 6.2 in the presence of 0.75 percent sodium chloride and 0.5 percent phenol, both weight per volume. Several lots of such fractionally precipitated protein were combined after being assayed for glucagon to give a blend of gluccagon source protein containing 3.60 percent by weight glucagon.

The glucagon assay procedure employed was an adaptation of the insulin immunoassay of Herbert, et al., J. Clin. Endocr., 25, 1375 (1965), using radioactive dilution and coated charcoal. Glucagon purity was taken to be the percent by weight of glucagon present, based on total solids. Total solids content was determined by known procedures. Furthermore, glucagon yield was taken to be percent glucagon relative to total glucagon originally present in the glucagon source protein.

EXAMPLE 1

A. Preparation of Glucagon Column Feed Solution

Glucagon source protein, 200 g, was dissolved in 5 liters of pH 3.0 aqueous hydrochloric acid. The pH was adjusted to about 11 with 3N aqueous sodium hydroxide solution in order to facilitate protein dissolution; the pH then was adjusted to 9.5 with 3N aqueous hydrochloric acid. The resulting solution was clarified by filtration. The final volume was 5.675 liters.

B. First Gel Filtration

A sectional chromatograhic column consisting of four Pharmacia KS-370/15 units (Pharmacia Fine Chemicals, Inc.) was packed with Sephadex G-50F (Pharmacia Fine Chemicals, Inc.) and equilibrated at 25° C with pH 9.5 aqueous ammonium hydroxide containing 0.001 M EDTA and 0.1 percent butanol. The glucagon column feed solution was applied to the column when then was eluted with the pH 9.5 aqueous ammonia/EDTA/butanol eluant at 300–400 ml/min. Protein was detected in the effluent by measuring eluant percent transmittance at 280 nm, using an LKB Uvicord II absorptiometer (LKB Produkter AB, Stockholm, Sweden). After collecting 19.6 liters of effluent (the volume being equal to the column void volume), a 22.4-liter fraction was collected which contained high molecular weight proteins. Three additional fractions then were collected as follows: (1) forecut eluant fraction, having a volume of 2 liters; (2) glucagon-containing eluant, having a volume of 11 liters; and (3) aftercut eluant fraction, having a volume of 4 liters. The pH of the glucagon-containing eluant was adjusted to 5.5 with 3N aqueous hydrochloric acid and the eluant was allowed to stand overnight at 25° C. Final eluant volume was 11.0 liters. The eluant contained 50.6 g total solids, equivalent to 4.6 mg/ml; glucagon content was 6.058 g, corresponding to 551 mcg/ml. Glucagon purity was 11.97 percent and the yield was 84.14 percent, based on a glucagon source protein glucagon content of 7.20 g.

C. Intermediate Crystallization

The glucagon-containing eluant obtained above was agitated and heated to 60° C. The pH was adjusted to 5.0 with 3N aqueous hydrochloric acid. The solution then was filtered while hot and the filtrate was chilled 24 hours at about 5° C to permit glucagon crystallization and settling. The mother liquor was separated from the glucagon crystals by first decanting and then centrifuging. The mother liquor was held for rework. The glucagon crystals were dissolved in pH 9.5 aqueous ammonia/EDTA/butanol and the resulting solution was filtered. The final solution had a volume of 1.65 liters and contained 6.27 g total solids, corresponding to 3.8 mg/ml. Solution glucagon content was 3.82 grams, corresponding to 2,322 mcg/ml. Glucagon purity now was 61.1 percent, and the yield, 53.1 percent.

D. Second Gel Filtration

A five-section chromatographic column similar to that described above was prepared. The solution obtained from the intermediate crystallization was added to the column and the column was eluted with pH 9.5 aqueous ammonia/EDTA/butanol eluant at 500 ml/min. Elution of the column proceeded essentially as described in B. above. In this case, the glucagon-containing eluant consisted of 14.0 liters. Such glucagon-containing eluant contained 5.6 g total solids, corresponding to 0.40 mg/ml. Glucagon content was 3.40 g, corresponding to 243 mcg/ml. Glucagon purity was 60.7 percent, and yield, 47.22 percent. It should be noted that, because of the various pH adjustments, eluant inorganic salt content had increased significantly. Because the inorganic salts have a $K_d$ approximately equal to that of glucagon, such salts are not removed from glucagon by gel filtration. Because glucagon purity is based upon total solids, the second gel filtration appears not to achieve any purification. Some separation of nonglucagon protein from glucagon has been accomplished, however. Stated differently, each step would show an increase in glucagon purity if such purity were based on total protein solids rather than total solids.

E. Final Glucagon Crystallization

The glucagon-containing eluant from the second gel filtration was adjusted to pH 7.5 with 20 ml of 10 percent aqueous phosphoric acid. The resulting solution was agitated at 5° C for 18 hours to permit maximum glucagon crystallization, and then was allowed to settle for about 72 hours. The mother liquor was separated by decanting and centrifuging, and held for rework. The glucagon crystals were successively washed, once with 0.001 percent saline, twice with absolute alcohol, and once with anhydrous ether. The crystals then were dried in vacuo overnight. The glucagon crystals thus obtained amounted to 3.455 g. Based upon amino acid analysis and cation exchange chromatography analysis, the glucagon had a purity of 91.1 percent. Accordingly, the glucagon crystals contained 3.13 g of pure glucagon, equivalent to a yield of 43.5 percent.

EXAMPLE 2

A. Preparation of Glucagon Solution

Glucagon source protein, 4,000 g, containing 144 g of glucagon, was dissolved in 250 liters of pH 2.8 aqueous hydrochloric acid. Dissolution was aided by stirring for 1 hour at 25° C, after which time the solution was filtered. To the solution were added 550 liters of water and sufficient 3N aqueous hydrochloric acid to give a pH of 2.1. The final solution volume was 800 liters.

B. Fibril Formation

To the solution thus obtained was added 3.2 liters of 0.1 M EDTA and 4.8 liters of 50 percent by weight aqueous ammonium sulfate. The resulting solution had a pH of 2.3. The solution was agitated for 48 hours at 27° C to induce fibril formation. The fibrils which formed were separated from the supernatent liquid by centrifugation. The fibrils were suspended in 120 liters of pH 2.0 aqueous hydrochloric acid containing 0.2 percent, weight per volume, of phenol; the pH then was adjusted to 10 with 10 percent aqueous potassium hydroxide solution. The final solution consisted of 122 liters, containing 683.2 g total solids, corresponding to 5.6 mg/ml. The solution contained 98.088 g of glucagon, corresponding to 804 mcg/ml. Glucagon purity was 14.36 percent, and yield, 68.12 percent.

C. Intermediate Crystallization

The pH of the glucagon fibril solution was adjusted to 7.0 with 10 percent aqueous phosphoric acid. The solution was heated to 60° C, during which time water was added to adjust the volume to 137 liters and the solids concentration to 5.0 mg/ml. The solution then was adjusted to pH 5.0 with additional 10 percent aqueous phosphoric acid and filtered hot. The filtrate was chilled at about 5° C for 72 hours. The mother liquor was removed by decantation and centrifugation, and held for rework. The glucagon crystals were dissolved in 9.0 liters of pH 9.5 aqueous ammonium hydroxide and the resulting solution was filtered. A 1-liter aliquot was withdrawn for Example 3, which aliquot represented 11.1 percent of the solution. The total 9-liter volume of glucagon solution contained 99.0 g total solids, corresponding to 11.0 mg/ml. Such solution also contained 42.11 grams of glucagon, corresponding to 4,679 mcg/ml. Glucagon purity was 42.54 percent, and yield, 29.24 percent.

D. Gel Filtration

The remaining 8 liters of glucagon solution was introduced onto a five-section column as described in Example 2.D. The sample was eluted in the manner already described at a flow rate of 350–500 ml/min. Elution progressed as described hereinabove. The glucagon-contained eluant fraction consisted of 30 liters, and contained 66.0 g total solids, corresponding to 2.2 mg/ml. Glucagon content was 36.84 g, corresponding to 1,228 mcg/ml. Glucagon purity was 55.8 percent, and yield (corrected for aliquot removal), 28.78 percent.

E. Final Glucagon Crystallization

The glucagon eluant fraction was adjusted to pH 7.5 with 0.1 liter of 10 percent agueous phosphoric acid. The solution was agitated at 5° C for 16 hours to permit glucagon cyrstallization and the crystals which formed were allowed to settle for about 72 hours. The mother liquor was separated by decantation and centrifugation, and held for reprocessing. The glucagon crystals were washed successively with 0.001 percent saline, absolute alcohol, and ether, and then were dried in vacuo. The glucagon crystals thus obtained weighed 33.654 g. Glucagon purity was estimated by amino acid analysis and cation exchange chromatography analysis to be 84.35 percent. Thus, total pure glucagon obtained amounted to 28.39 g, which corresponded to a 22.17 percent yield.

EXAMPLE 3

The one-liter aliquot of the glucagon fibril solution prepared in Example 2.C. was adjusted to a slightly hazy condition at pH 7.8 with about 300 ml of 10 percent aqueous phosphoric acid. The solution then was agitated for about 2 hours at 25° C and then for about 16 hours at 5° C. The glucagon crystals which formed were allowed to settle for about 72 hours. The mother liquor was separated by centrifugation and held for rework. The glucagon crystals were washed successively with saline, absolute alcohol, and ether, and then were dried in vacuo. The glucagon thus obtained amounted to 3.897 g. Glucagon purity was determined to be 81.5 percent by amino acid analysis and cation exchange chromatography analysis. Thus, the actual yield of glucagon corresponded to 3.341 g or 21.09 percent.

From the examples, it is clear that the process of the present invention provides higher purity glucagon in higher yield than the most preferred prior art procedure, even when such procedure is coupled with a gel filtration step.

A better understanding of the process described in Example 1 will be had by referring to the drawing. The drawing is an elution diagram or profile which is characteristic of either of the gel filtration steps in Example 1. The drawing consists of a plot of the absorbance at 280 nm of various fractions vs. effluent volume in liters and of a plot of the glucagon content of selected fractions vs. effluent volume in liters. Thus, the diagram indicates both protein content and glucagon content of the effluent collected during the course of elution. From the diagram, it is clear that glucagon is eluted in a relatively sharp band, even though other proteins are continuously passing through the column.

From the foregoing specification, it will be clear to one having ordinary skill in the art that optimum conditions for the purification of any given impure glucagon, although varying from case to case, can be readily determined.

What is claimed is:

1. A process for purifying glucagon which comprises the steps of
   A. swelling a gel having in the dry state a water regain of at least about 4 percent by weight and particle diameters smaller than about 100 microns;
   B. packing a column with the swollen gel;
   C. adding to the packed column an aqueous solution, having a pH of from about 9 to about 11, of glucagon having a purity of at least about 0.1 percent, wherein such glucagon solution contains at least about 0.01 miligrams of glucagon per mililiter of solution and less than about 10 percent, weight per volume, total protein solids, and the total amount of glucagon added to the column is sufficient to provide a column loading of from about 0.01 to about 5 g per liter of bed volume; and
   D. eluting the glucagon from the column at a temperature from about 4 to about 40° C., with an aqueous eluant having a pH within same range as that of the glucagon solution.

2. The process of claim 1, wherein said gel has a water regain in the range of from about 4 to about 98 percent.

3. The process of claim 2, wherein said gel has a water regain in the range of from about 5 to about 20 percent.

4. The process of claim 3, wherein said gel is a cross-linked dextran.

5. The process of claim 4, wherein said gel has a water regain of about 5 percent.

6. The process of claim 5, wherein the particle diameters of said gel are in the range of from about 20 to about 80 microns.

7. The process of claim 1, wherein the column loading is in the range of from about 0.08 to about 3.1 g per liter of bed volume.

8. The process of claim 1, wherein the eluant contains up to about 0.01 moles per liter of a divalent metal ion chelating agent of the formula,

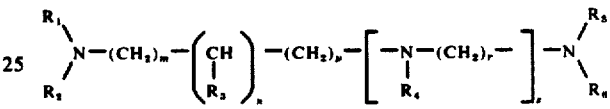

wherein $R_1$ and $R_5$ are monovalent organic radicals independently selected from the group consisting of carboxymethyl, carboxyethyl, $C_1$–$C_6$ alkyl, and $C_1$–$C_6$ hydroxyalkyl; $R_2$ and $R_6$ are monovalent organic radicals independently selected from the group consisting of carboxymethyl and carboxyethyl; $R_3$ is a monovalent radical selected from the group consisting of hydrogen, hydroxy, and $C_1$–$C_6$ alkyl; $R_4$ is a monovalent radical selected from the group consisting of hydrogen, carboxymethyl, and carboxyethyl; $m$ is an integer from 1 to 6, inclusive; $n$ is an integer which is either 0 or 1; $p$ is an integer which is either 0 or 1; $r$ is an integer from 2 to 6, inclusive; and $s$ is an integer from 0 to 2, inclusive.

9. The process of claim 8, wherein such chelating agent is ethylenediamine-N,N,N',N'-tetraacetic acid.

10. The process of claim 1, wherein the eluant contains up to about 0.5 percent by volume of butanol as stabilizer.

11. The process of claim 10, wherein the amount of butanol present 0.1 percent by volume.

12. The process of claim 1, wherein elution is carried out at ambient temperature.

* * * * *